US010278893B2

(12) United States Patent
Parker

(10) Patent No.: US 10,278,893 B2
(45) Date of Patent: May 7, 2019

(54) BOTTOM ENTRY SAUNA, STEAM ROOM, STEAM EGG

(76) Inventor: Michael G. Parker, Los Angeles, CA (US)

(*) Notice: Subject to any disclaimer, the term of this patent is extended or adjusted under 35 U.S.C. 154(b) by 432 days.

(21) Appl. No.: 13/589,788

(22) Filed: Aug. 20, 2012

(65) Prior Publication Data

US 2013/0042402 A1 Feb. 21, 2013

Related U.S. Application Data

(60) Provisional application No. 61/525,157, filed on Aug. 18, 2011.

(51) Int. Cl.
*A61H 33/06* (2006.01)
*A61N 5/06* (2006.01)

(52) U.S. Cl.
CPC ....... *A61H 33/066* (2013.01); *A61H 2201/10* (2013.01); *A61H 2201/102* (2013.01); *A61N 2005/064* (2013.01); *A61N 2005/0652* (2013.01); *A61N 2005/0663* (2013.01); *A61N 2005/0668* (2013.01)

(58) Field of Classification Search
CPC ............... A61H 33/066; A61H 33/06; A61H 2033/068; A61N 2005/064; E04H 9/145; E04B 2001/0061
USPC ...... 4/524; 52/79.1, 194, 80.1, 81.6; 135/87, 135/901
See application file for complete search history.

(56) References Cited

U.S. PATENT DOCUMENTS

| | | | | |
|---|---|---|---|---|
| 871,074 A * | 11/1907 | Stockton | ................. | 601/11 |
| 1,979,094 A * | 10/1934 | Blunt | ................. | 4/527 |
| 2,967,494 A * | 1/1961 | Rosenfeld | ................. | E04H 9/10 109/1 S |
| 3,271,786 A * | 9/1966 | Joy | ................. | 4/532 |
| 3,368,575 A * | 2/1968 | Besonen | ................. | 135/147 |
| 3,419,915 A * | 1/1969 | Clark, Jr. | ................. | 4/526 |
| 3,422,465 A * | 1/1969 | Jones et al. | ................. | 4/532 |
| 3,889,698 A * | 6/1975 | Roessl | ................. | 135/94 |
| 4,277,855 A * | 7/1981 | Poss | ................. | A61H 33/06 4/524 |
| 4,796,649 A * | 1/1989 | Tolomay | ................. | 135/137 |
| 4,833,739 A * | 5/1989 | Sakakibara et al. | ................. | 4/524 |
| 5,416,931 A * | 5/1995 | Wolfenden et al. | ................. | 4/524 |
| 5,628,073 A * | 5/1997 | Popovich | ................. | A61H 33/06 135/115 |
| 5,645,578 A * | 7/1997 | Daffer et al. | ................. | 607/91 |
| 6,497,717 B1 * | 12/2002 | Daffer et al. | ................. | 607/83 |

(Continued)

*Primary Examiner* — Janie M Loeppke
(74) *Attorney, Agent, or Firm* — Gazdzinski & Associates, PC

(57) ABSTRACT

The invention disrupts the paradigm of the side entrance within the field of saunas, steam rooms and therapeutic chambers. The invention reorients the entrance from a door in the side of a therapeutic chamber, as is the situation in the prior art, and places the point of ingress and egress to the bottom or floor of the chamber. Without a side entry door, much less heat is lost when individuals enter and exit the chamber. Furthermore, this invention creates the opportunity for 360 degree seating in steam rooms and saunas, which is exemplified in the embodiment of the prototype named Steam Egg, which is a ten and a half foot tall freestanding egg shaped, mirror covered, steam room that is entered through a hole in the bottom, hovering 33.5 inches off the ground stabilized on three steel legs.

18 Claims, 8 Drawing Sheets

(56) References Cited

U.S. PATENT DOCUMENTS

| | | | |
|---|---|---|---|
| 6,938,381 B1* | 9/2005 | Villa | E04B 1/3211 |
| | | | 52/79.1 |
| 7,188,635 B2* | 3/2007 | Johnson | A01M 31/02 |
| | | | 135/87 |
| 7,503,926 B2* | 3/2009 | Daffer et al. | 607/81 |
| 9,309,662 B2* | 4/2016 | Vazquez | E04B 1/34352 |
| 9,440,041 B1* | 9/2016 | Lacayo | A61M 16/14 |
| 2013/0014791 A1* | 1/2013 | Hill | E04H 9/028 |
| | | | 135/93 |
| 2017/0246080 A1* | 8/2017 | Monterenzi | A61M 11/02 |

* cited by examiner

US 10,278,893 B2

BOTTOM ENTRY SAUNA, STEAM ROOM, STEAM EGG

CROSS-REFERENCE TO RELATED APPLICATIONS

This non-provisional utility patent refers to the provisional patent application number U.S. 61/525,157 filed on Aug. 18, 2011 by the small entity independent inventor, Michael G. Parker in Los Angeles, Calif. 90013.

PRIOR ART U.S. PATENT DOCUMENTS CITED

U.S. Pat. No. 871,074
Nov. 12, 1907
Stockton
Bath Apparatus
U.S. Pat. No. 1,979,094
Oct. 30, 1934
Blunt
Knock-Down Heat Bath Appliance
U.S. Pat. No. 5,628,073
May 13, 1997
Popovich
Sauna
U.S. Pat. No. 3,271,786
Sep. 13, 1966
Joy
Portable Sauna Cabinet
U.S. Pat. No. 3,368,575
Feb. 13, 1968
Besonen
Portable Collapsible Shelter
U.S. Pat. No. 3,419,915
Jan. 7, 1969
Clark
Heat Bath Appliance
U.S. Pat. No. 3,889,698
Jun. 17, 1975
Roessl
Portable Shelter
U.S. Pat. No. 4,277,855
Jul. 14, 1981
Poss
Portable Sauna
U.S. Pat. No. 3,422,465
Jan. 21, 1969
Nylin
Prefabricated Sauna Room
U.S. Pat. No. 4,796,649
Jan. 10, 1989
Tolomay
Ice Fishing Shelter
U.S. Pat. No. 5,416,931
May 23, 1995
Wolfenden et al.
Booth
U.S. Pat. No. 4,833,739
May 30, 1989
Sakakibara et al.
Steam Sauna
U.S. Pat. No. 6,497,717
Dec. 24, 2002
Daffer et al.
Therapy steam and heat treatment cabinet
U.S. Pat. No. 7,503,926
Mar. 17, 2009
Daffer et al.
Combined sauna and environmental capsule
U.S. Pat. No. 5,645,578
Jul. 8, 1997
Daffer et al.
Total Therapy Sauna Bed System

STATEMENT REGARDING FEDERALLY SPONSORED RESEARCH OR DEVELOPMENT

Not Applicable

REFERENCE TO A SEQUENCE LISTING, A TABLE, OR A COMPUTER PROGRAM, LISTING COMPACT DISC APPENDIX

Not Applicable

BACKGROUND OF THE INVENTION

For thousands of years humans have heated enclosed spaces designed for the purpose of entering singularly or communally, for the beneficial health properties thought to result from periods of high heat. The ancient Roman and Turkish baths, the Mesoamerican temazcals, the Native American sweat lodges, the contemporary Finnish saunas, Korean jimjilbangs, and prefabricated and portable saunas such as those referenced in U.S. Pat. Nos. 1,979,094, 5,628,073, 4,277,855, 3,422,465, 4,833,739, are examples that are relevant to the history and field of the endeavor to which this invention pertains. Up until now, though, dry and wet saunas and various therapy rooms, such as vibratory, aromatherapy, chromotherapy, have either had entrances in the form of side doors, or in the cases of recent portable chambers, the capsule has been closed or zippered around the individual. The prior art's points of ingress and egress permits heat to escape every time the door is opened because the door is at the same level as the heated chamber. Additionally, a side entrance reduces the area available for seating or lying. Unlike a cedar hot tub, for example, which allows 360 degree seating because it is entered from above, the side door in prior art generally creates unidirectional, duodirectional or tridirectional bench seating, but cannot provide for seating fully in the round.

BRIEF SUMMARY OF THE INVENTION

The Bottom Entry Sauna, Steam Room, Steam Egg presents a solution to the heat loss of the prior art due to side entrances, and presents a solution to create a 360 degree seating solution such that people can enjoy facing one another, as is popular in hot tubs. The solution to this previously existing problem in prior art is locating the point of ingress and egress on the bottom or floor 1 of the structure, chamber, room, housing that contains the therapeutic 2 enclosed space. By lifting the sauna or other therapeutic room, off of the ground level (that the structure exists within; either indoors or out of doors) a few feet or more, making an aperture for entry and exit 1, solves the existing problem of the prior art's heat loss. Simply and clearly stated, since heat rises, if the door is located on the floor of the therapeutic chamber 1, heat is not lost when individuals enter or exit. Additionally, for those individuals who enter and exit a heated therapeutic room after just a few minutes, those who stay for twenty or more minutes often become frustrated with those who are quick to enter and soon thereafter exit, as it cools down the room with every ingress and egress. This invention removes this frequent frustration, thus creating more positive feelings among those who can handle the heat for both short and long durations.

Additionally, in a bottom entry therapeutic structure there is roughly 20% to 30% more usable seating area gained by locating the door on the floor 1, such that people can steam or engage with other therapies, singularly or in multiple, such as chromotherapy, in such a way that people can look at each other directly in 360 degrees, creating a more sociable and direct human interaction, like that of a dinning table FIG. 7.

The first realized embodiment, referred to herein and in-depth in the provisional patent U.S. 61/525,157 submitted to the USPTO on Aug. 18, 2011, titled Bottom Entry Sauna, Steam Room and Steam Egg, is a ten and a half foot tall, six and a half foot diameter, egg shaped steam room supported 33.5 inches off the ground with three equidistant steel legs, that is structured with steel and expanded poly styrene (EPS), and surfaced on the interior with a surface of thinset mortar and an exterior surface of approximately 2000 three inch square mirrors FIG. 1-8. The interior can fit eight adults sitting in a circle facing one another. Their feet sit on a four-inch footrest ledge 11, which circles the 22-inch diameter hole 1 that functions as the ingress and egress point. Throughout a few hours of steaming, fifty or more people can enter and exit the therapeutic chamber without ever having to open or close a single door, and with much less energy required to maintain a constantly therapeutic environment. In fact the point of ingress and egress remains open 1—a door or shutter was never needed after the initial test proved the theory that a door would be unnecessary. Note, that the present embodiment described herein has been tested in weather conditions as low as 40 degrees Fahrenheit and no door was needed, but it is within the intent of the invention that if a bottom entry chamber is sited in a consistently colder environment that a Velcro style hinged door may be required to mitigate extreme temperatures and wind shear. Many people complain saunas with side doors produce feelings of claustrophobia—since the bottom perture remains open 1, a visual and physical connection to the outside is kept—while sitting in Steam Egg, people often describe that looking at pairs of feet silhouetted in the bottom entrance is a camp-fire-like visual effect.

BRIEF DESCRIPTION OF THE SEVERAL VIEWS OF THE DRAWING

The drawings herein, are based on the present embodiment, which during its creation seemed the best embodiment by the inventor. This egg shaped embodiment is called Steam Egg, but the claims of this invention are not limited to the formal shape, scale, nor materials of this embodiment of the Bottom Entry Sauna, Steam Room, Steam Egg. The embodiment presented in the figures demonstrates to those of ordinary skill in the pertinent art so they can make and use, without extensive experimentation, a bottom entry therapeutic chamber based on the current embodiment or future embodiments of, but not limited to, a bottom entry therapeutic, restorative, or meditative chamber.

DETAILED DESCRIPTION OF THE INVENTION

Figure 1:
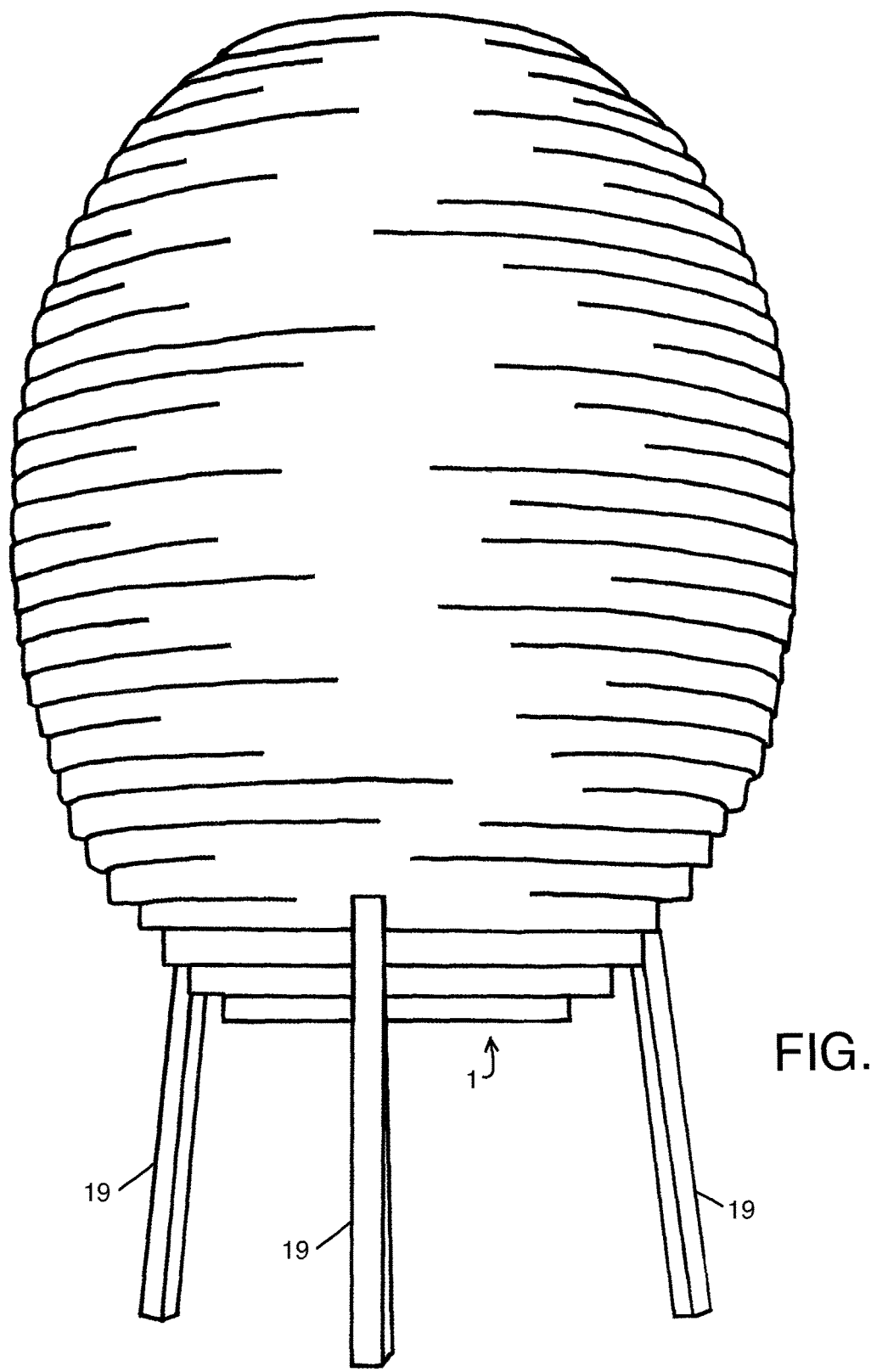
FIG. 1 is an exterior view of the Steam Egg embodiment
Figure 2:
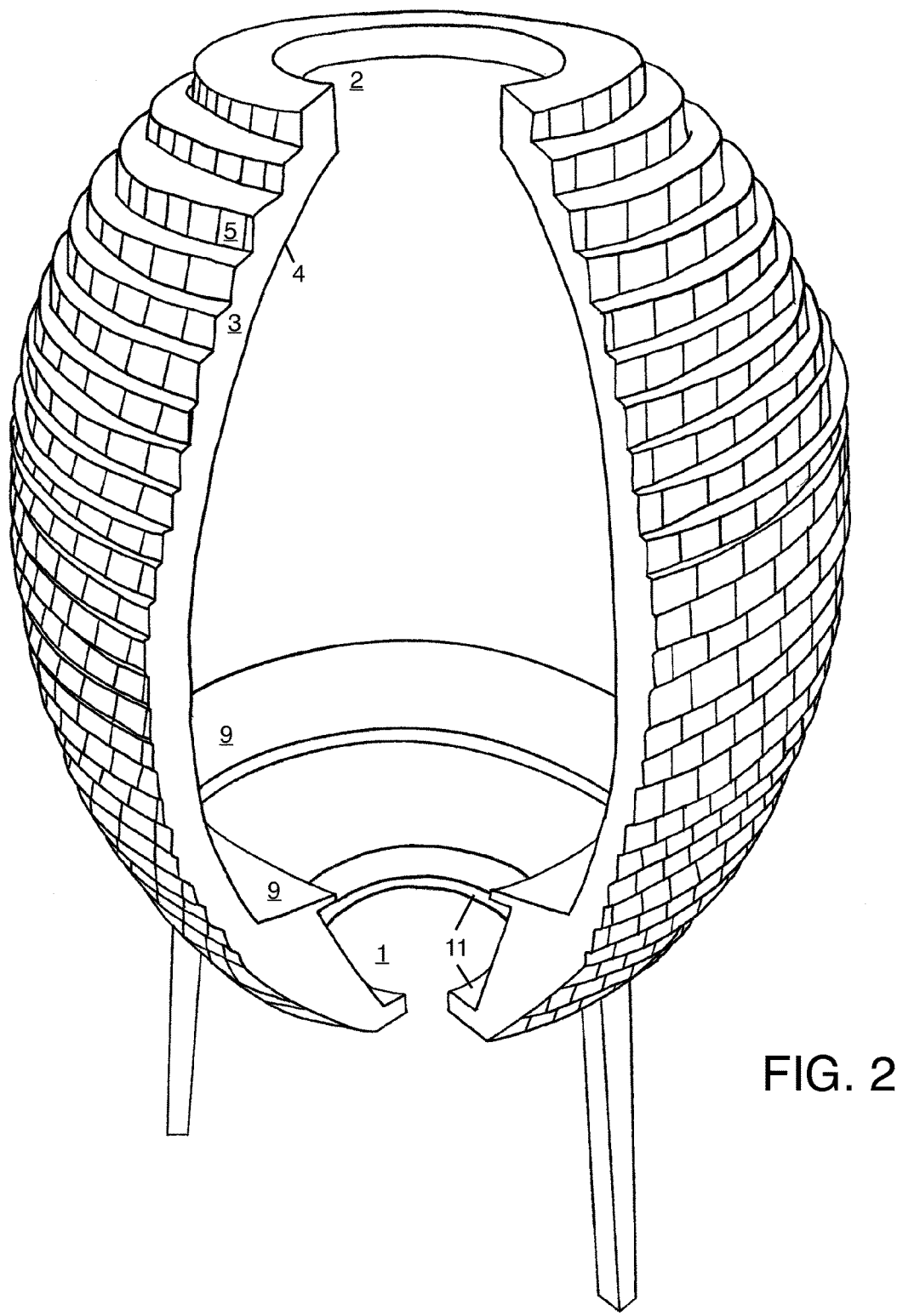
FIG. 2 is an exterior view of the Steam Egg, in a partly broken away perspectival view from above and to the side, that show the interior chamber and the elevations of the structure.
Figure 3:
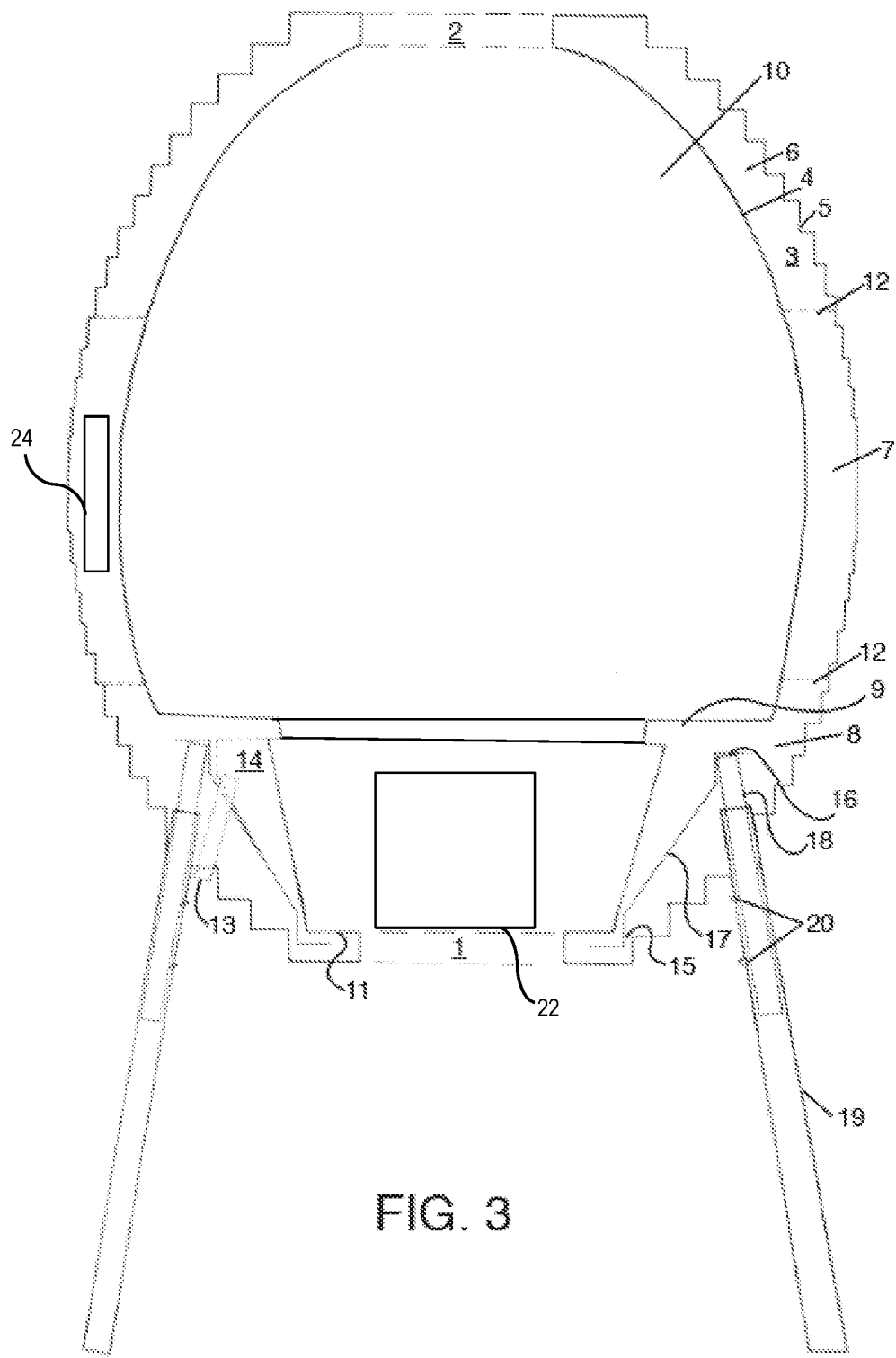
FIG. 3 is a detailed plan view with all parts labeled 1-20 with reference characters
Figure 4:
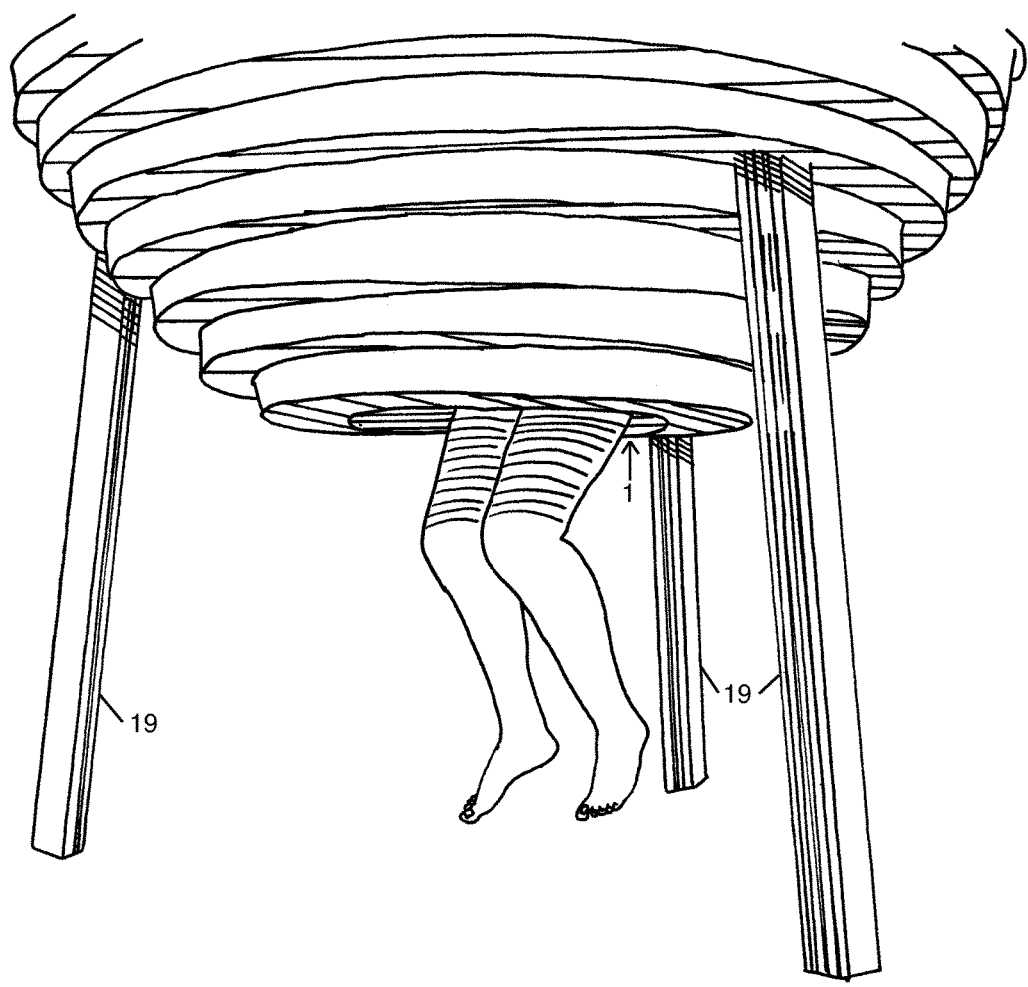
FIG. 4 shows a side view, from the perspective of someone crouching down about ten feet from the embodiment, of an individual getting into the bottom entry therapeutic chamber.
Figure 5:
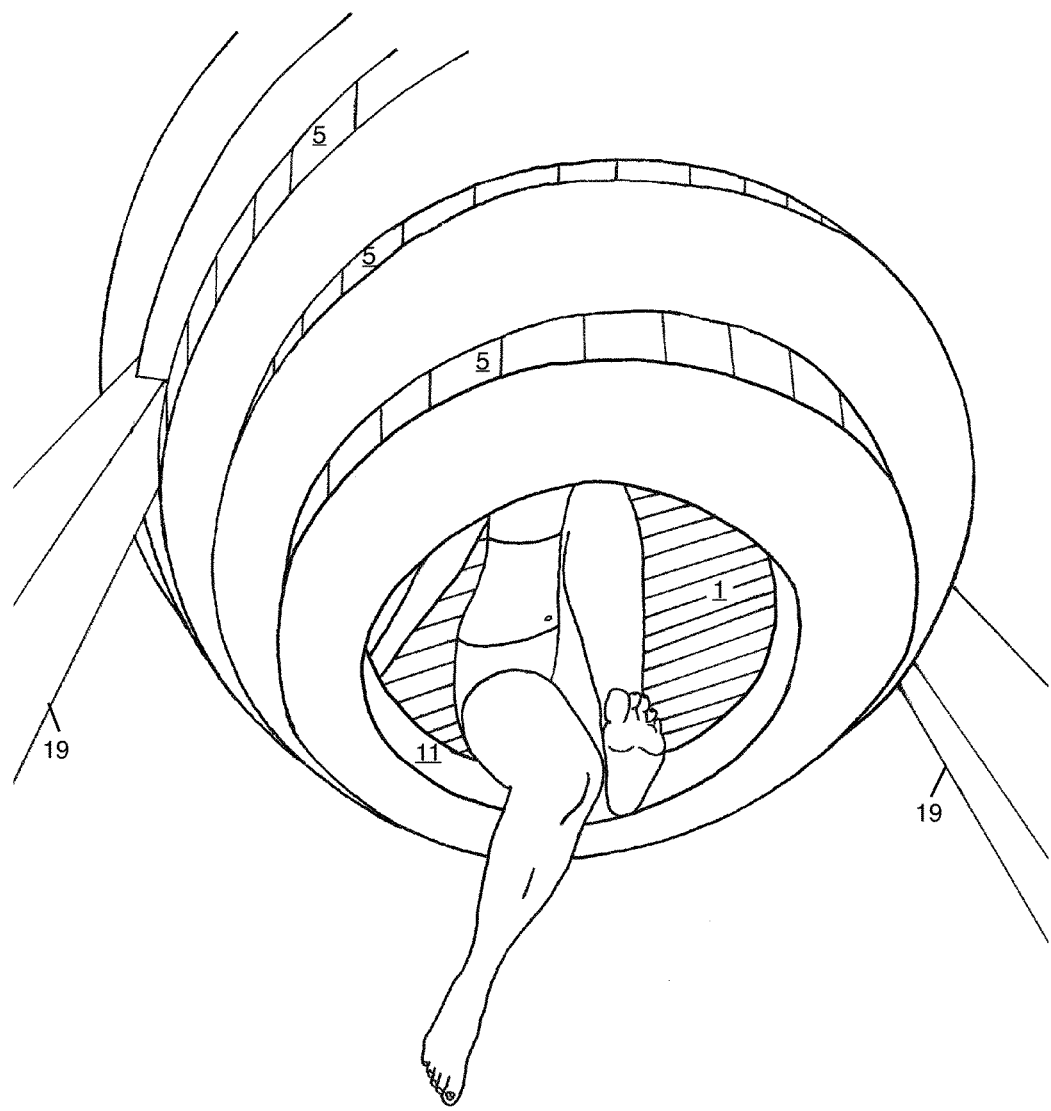
FIG. 5 shows a view looking up into the bottom entry hole as an individual lifts herself inside the therapeutic chamber
Figure 6:
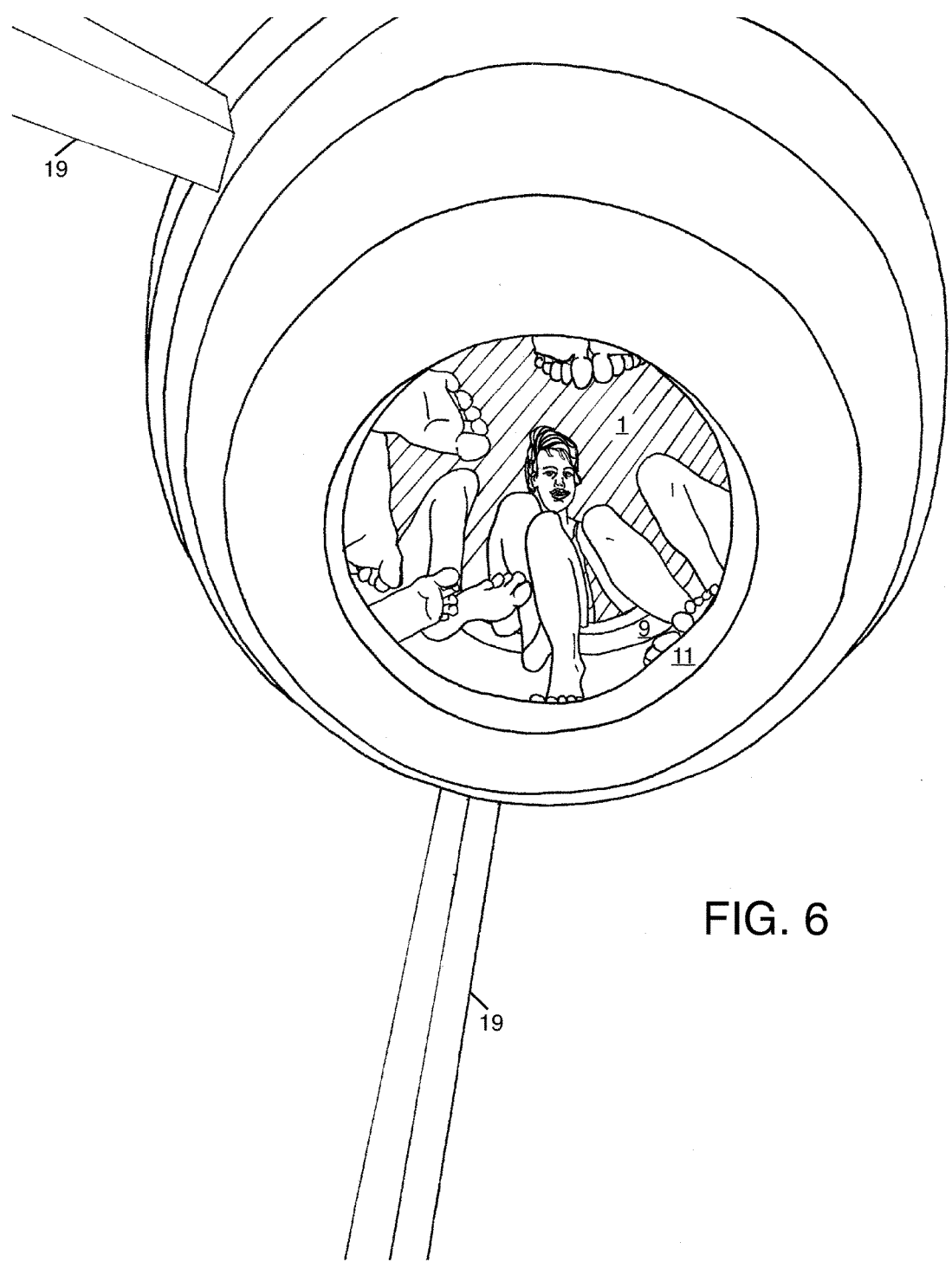
FIG. 6 shows the view looking up into the bottom entry hole with four individuals already inside.

The bottom entry sauna, steam room, steam egg, or therapeutic room consists of a structural shift in relocating the paradigm of the ingress and egress points into a therapy room so that the ingress and egress door becomes located on the floor 1 of said structure FIG. 1-8. The invention rose out of the desire to solve the problem of wasted energy loss and wasted space in the field of saunas and therapy chambers. The prior art's side door entry allows much heat to escape each time the door opens and closes. The prior art's side door also reduces the quantity of seating available within these generally small heated spaces. The invention of the Bottom Entry Sauna, Steam Room, Steam Egg solves these problems and lays a foundation for future improvements in the use of these forms, but not limited to other restorative and health promoting chambers, as requirements for energy efficiency and space efficiency become more attractive to both consumers and producers. The first embodiment FIG. 1-8 of the bottom entry advancement is in the form of an egg-shaped steam room supported on three legs 19 surfaced on the interior with mortar 4 and on the exterior with three-inch square mirrors 5. The first embodiment fits up to eight adults, and has been used by hundreds of people who fondly call it Steam Egg. The drawings herein refer to this embodiment but the claims can be embodied in multiple forms, shapes, sizes, and materials, which fits within the spirit of this invention, that includes the ingress and egress points at the floor of the structure or chamber 1, that is for the purpose of therapy in the form of, but not limited to, dry heat or steam.

The invention's first embodiment is a steam sauna that is a freestanding form, which is entered from the bottom FIG. 1-8. This prototype, which is drawn herein, stands 10.5 feet tall. This embodiment is an egg-shaped steam room with a mirrored exterior 5. The sauna is entered through a 22" hole in the bottom 1 of the form, that is also the 4" wide circular footrest 11 between its three legs 18, 19. Upon entrance there is a 360-degree 5' diameter bench seat 9 capable of fitting eight adults. The interior is surfaced with a high quality thinset mortar 4. The interior form is domed creating a live acoustic environment 10. The overall egg-form is eight feet from the bottom to the top FIG. 1. Steam is released from a vent underneath the bottom of the bench seat 13. This prototype has a round opening at the top of the interior 2 with equal dimensions to the entrance at the bottom 1. The top aperture 2 is closed when the steam is on to trap the steam with a double layer of standard thickness towels.

When steam is not on, the interior space 10 is a softly lit contemplative and acoustically live space. The bottom entrance 1 to the prototype remains open throughout steaming (since steam rises). Keeping the entrance located at the bottom reduces heat loss from side-entry doors present in prior art sauna designs. The discovery that the entrance can remain open is a breakthrough in steamer user experience. Plus many complain that typical saunas produce feelings of claustrophobia—the bottom remaining open keeps a visual and physical connection to the outside—while sitting in Steam Egg, people often describe that looking at pairs of feet silhouetted in the bottom entrance is a camp-fire-like visual effect FIG. 6-7. Also, the mirrored exterior 5 gives the steamer an unclear sense of the scale of this embodiment, such that once people are inside the individual has a feeling of protective, yet unbounded space due to the rounded forms and lack of hard edges 4. Multiple hundreds of people of various ages and sizes, from children to the elderly, have thoroughly tested the embodiment demonstrated in the figures herein.

Key advantages of the bottom entry sauna include, but are not limited to the following: This advancement requires less energy to maintain a heated interior environment. When people enter and then leave after only a few minutes due to it being too hot for them, the other people already in the heated room do not suffer decreasing fluctuations to the temperature of their heated environment 10. In the prior art first time sauna goers who come in for only a few minutes frequently frustrate sauna enthusiasts. This frustration can lead the enthusiast to feel upset with the new person as the heat decreases every time the door is opened. The prior art does not have a solution to keep heat from escaping when people come and go. The bottom egress and ingress 1 makes for an atmosphere where individuals can coexist happily between those who enjoy the chamber for both short durations or long durations. The advancement herein from the prior art solves this existing problem of heat loss, wasted energy, and frustration thus increasing the overall user experience.

The current embodiment requires only two cloth towels to cover the upper hole 2 during a steaming session to keep the hot air inside. If the current embodiment becomes too hot, the cloth cover is easily popped open for one or more seconds to release some of the heat that is captured. Another advantage of the top cloth aperture covering is that you can add essential oils to the cloth, which can introduce another form of aromatherapy into the chamber 10. At the end of a steam session's present embodiment one stands on the bench 9 and easily reaches up and removes the cloth that is covering the hole 2. In a matter of seconds, the heat escapes from the interior through the top hole drafting cool air through the bottom hole 1 creating a vertical column of uplifting cool air. This rush of cold air is an invigorating experience for the users, and unfamiliar within the field of prior art FIG. 8. This straight forward and not overly complicated solution of venting the wet sauna, creates a situation where the steam sauna is easy to clean, because the moisture vents out the top, making the chamber completely dry within 24 hours even in humid weather.

Figure 7:
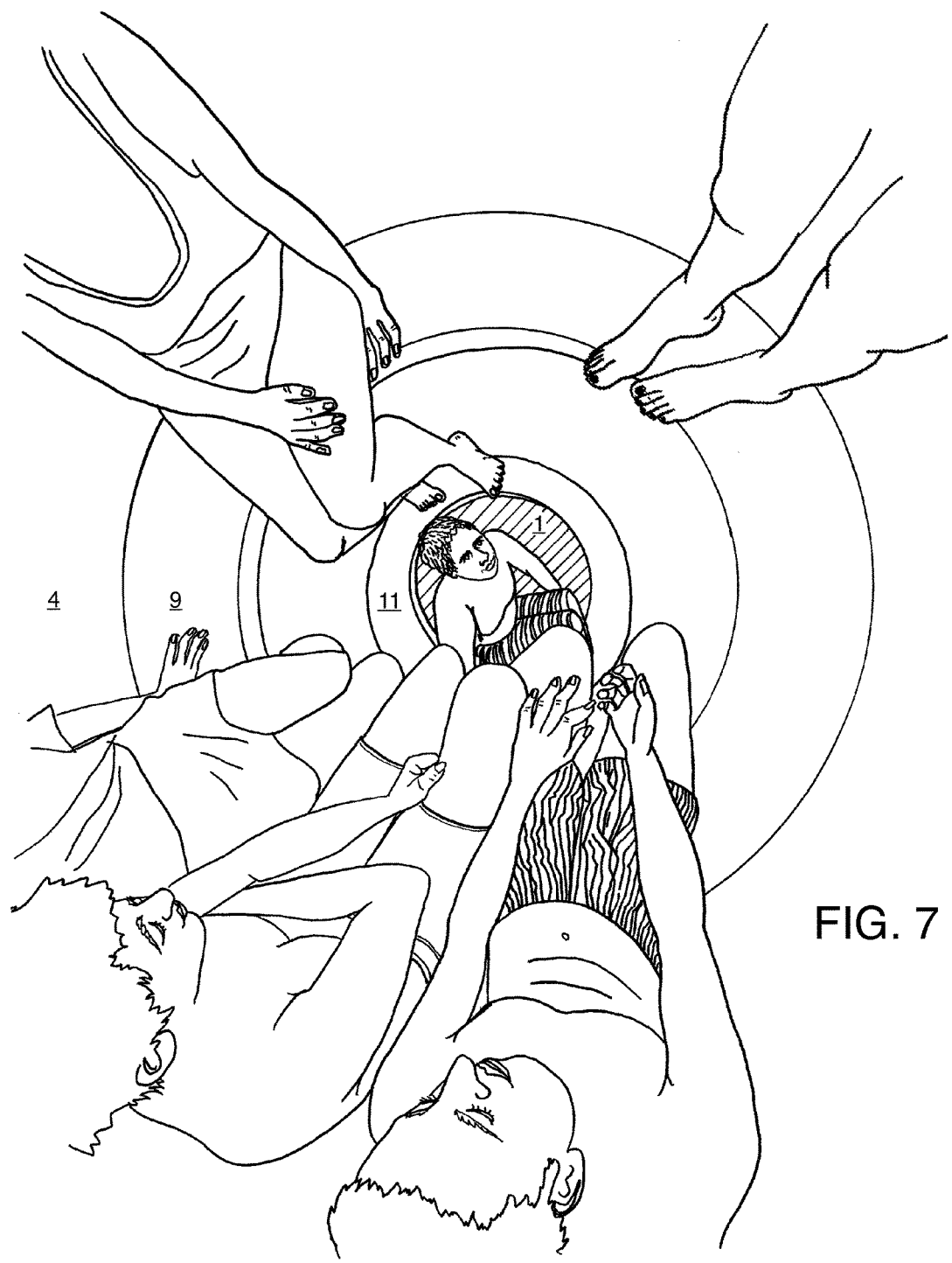
FIG. 7 shows the view looking down from someone standing inside the steam egg as someone begins to climb through the bottom point of ingress and egress, such that the sauna will soon be seating six persons
Figure 8:
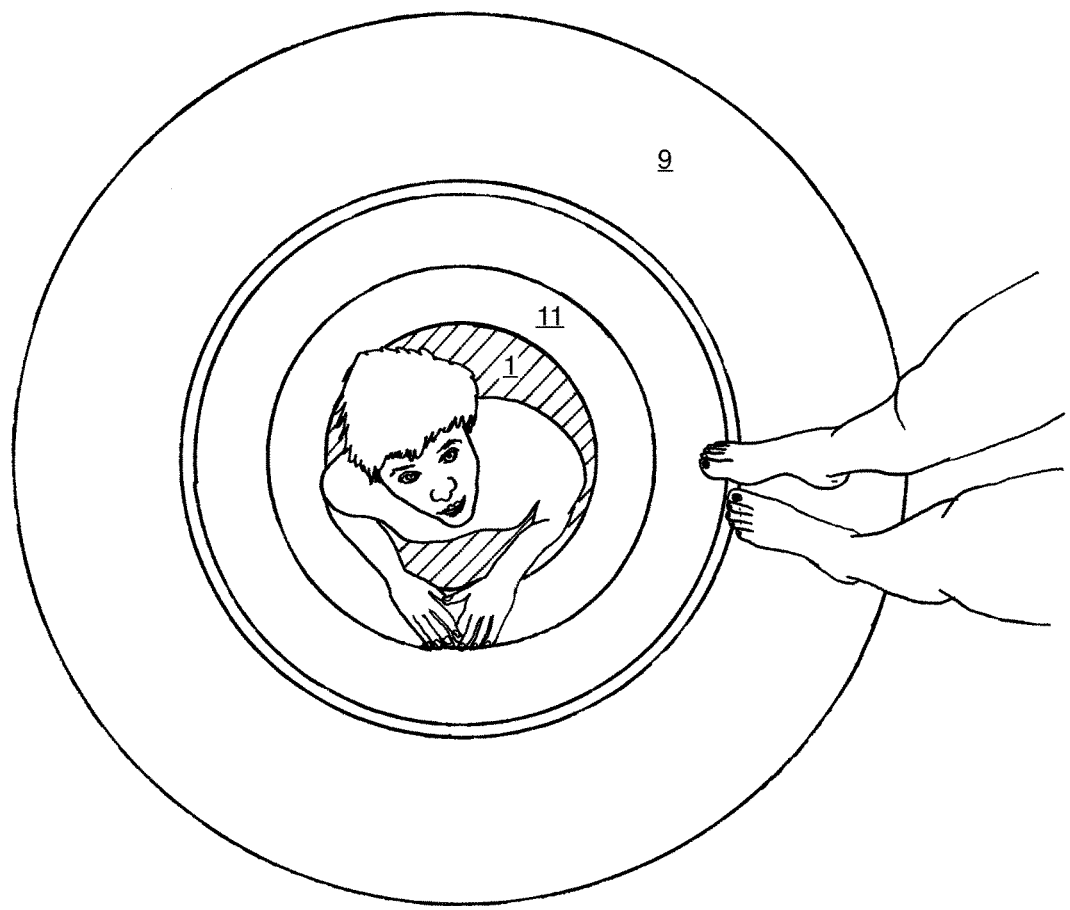
FIG. 8 shows the view looking down from someone standing inside the steam egg as the last person, besides the viewer, exits and looks back at the standing person after the steam was turned off and the column of cool air rose through the steam egg.

In addition to needing less energy to heat a bottom entry chamber, key to this invention is that it creates an opportunity for fully 360° seating within this field of art FIG. 7. There is no door or entry area taking up a section of the wall space. This creates the opportunity for individuals to sit fully in a circle, much like people would sit facing each other at a round dining table. The success of 360° seating in a closely related field is exemplified in the popularity of cedar hot tubs. Humans, for the most part, enjoy facing one another when engaging in social situations, and this invention's first embodiment has been rigorously tested with groups of people who do, indeed enjoy the capacity for 360° seating while steaming FIG. 7-8. In future embodiments, such that, but not limited by, where the scale increases, the capacity for fully rounded seating will surely be an attractive benefit. Enthusiasts of the first embodiment have specifically mentioned that typical social anxiety between individuals is broken by the seemingly borderless space within the interior of this embodiment. Additionally, the fact that no corners need to exist in the bottom entry chamber makes it possible that a greater number of people can sweat in a smaller cubic footage, than that of the side entry of prior art. This reduces energy costs.

The following description of the first embodiment is provided to enable any person skilled in the art to make and use the invention and to set forth the best mode contemplated by the inventor of carrying out this invention. Those skilled in the art will appreciate that various adaptations and modifications of the described preferred embodiment could be configured without departing from the scope and spirit of the invention. Therefore, it is to be understood that, within the scope of the appended claims, the invention may be practiced other than as specifically described herein.

The prototype was built from 33 six-inch thick by three-inch tall rings of expanded polystyrene (EPS) 3. These rings or circles were of necessary diameters to make an 8' tall egg-shaped form FIG. 1 that would sit on three equidistant legs 19. The rings were glued using expanding foam into three sections: a lower section including bench 8, a middle section 7, and a top section 6. Two steel rings 15, 16 made from 2"-¼" angle iron make the lower section structurally strong. One rings fits below the bench 16 and the other is located within the bottom portal and the footrest 15. Straight angle iron 17 is welded to connect the two steel rings 15, 16. Male legs of 2.5"-³⁄₁₆" square tubing 18 were welded to the rings and connectors (these three legs 18 extend four inches below the lower section 8 of the egg shape). This steel structure was then bonded to the lower section 8 (of the foam egg shape) with structural expanding foam. A 360-degree bench seat 9 was constructed of 2" thick galvanized EPS structural insulated panels (SIPS). Longer legs 19 (47" in length) of 3"-³⁄₁₆" steel material fit over the welded male 2.5" legs. These removable longer legs use bolts 20 to secure it to the welded structure. The prototype's legs make it so the lowest point of the egg-form is 33.5" from the ground. The three sections 6, 7, 8 of this embodiment are connected with keyed points 12. Building the sauna in three sections 6, 7, 8, with removable legs 19, and out of EPS 3 makes the sauna transportable by the physical strength of four adults. Future embodiments of the Steam Egg form will be even more easily transportable, and more easily installable.

The interior surface is shaped directly into the foam 3 creating a smooth rounded form—similar in shape to that of the interior of an eggshell. The foam is then surfaced with a layer of high quality thinset tile mortar 4. Layers of fiberglass screen were worked into the thinset mortar to create strength and flexibility. The initial layers of screen and mortar 4 connect the three sections of the egg form 6, 7, 8. The final interior surface 4 has a gritty-yet-scratch-free, slip-free quality reminiscent of California's desert granite. Approximately two thousand 3"×3" mirrors 5 are attached to the exterior's vertical surfaces of the exterior's stepped egg form 6, 7, 8.

This first embodiment has steam enter the chamber from a single 2" copper pipe 13 underneath an alcove recess 14 of the bench. Future embodiments can have multiple points, but are not limited by, for steam, dry heat, aromatherapy, light or sound vented in from underneath the cavity beneath the bench. For example, a standard steam generator can be connected externally or even fit within the cavity under the bench. The embodiment pictured has a steam generator that is not within the egg's form, and thus not pictured. Any appropriate form of steam generator can be hooked into the copper pipe 13. This embodiment used pots of boiling water and herbal teas located just outside of the egg on the floor to generate steam and aromatherapy, which vented into the copper pipe 13. Stereo sound in this prototype was pumped through a speaker located above the towel covered top aperture 2 and the bottom entry aperture 1.

Those skilled in the art will appreciate that various adaptations and modifications to the above-mentioned embodiment, referred to in the figures, will remain readily apparent when the generic principles of the present invention have been defined herein specifically to provide a bottom entry therapeutic structure. Therefore, it is to be understood that, within the scope of the appended claims, the invention may be practiced in other means than as specifically described herein.

The shape of the freestanding sauna room is herein drawn as a mirror covered egg shape, but the invention, the bottom entry therapeutic chamber, can be utilized in any number of three-dimensional forms encapsulating any number or methods of therapy rooms. The shape for example can be a balloon or a coconut or a sphere or a cube or a pyramid shape or a seven-sided shape or any number of planes or compound curves. The scale of the three-dimensional shape can range from where it fits one person to where it can fit multiple people; the embodiment in the figures can fit eight adult humans, with their knees gently touching in a circle. For a public sauna or spa the form might be better suited in certain circumstances to be so large that it can fit 20 or more people, with one or more rows of benches. This invention does not preclude or exclude larger size forms or shapes fitting any number of people. Other three dimensional forms of a bottom entry therapy structure may require additional structural planning. For example, but not excluding things not said herein include, four or more legs or a ladder like one in a swimming pool.

It is important to note that the design of the seating is pertinent to the embodiment presented in the figures, but that other imagined embodiments of this bottom entry invention, do not necessitate the inclusion of 360° seating 9. An embodiment can be envisioned such that one quarter of the bench is dedicated to a traditional dry sauna heating element 22. The preferred embodiment though, is to use a small heating element 22 for dry saunas underneath the bench.

Other imagined, preferred and non-limiting embodiments include plumbing and electrical 24 within the structure of the legs 18, 19 and walls 3. This can allow for easy utilization that is found in prior art found in therapeutic chambers such as showers, misting sprays, vitamin treatment therapy, chromotherapy, lighting design (likely in the form of waterproof LEDs), built in speakers, exhaust fans, other forms, shapes and styles of upper vents, remote controlled temperature controls to name just a few options available in future embodiments.

There are countless embodiment options for forming a structure that can be entered from a hole in the bottom 1. The structure of the bottom entry therapeutic chamber can be made out of multiple materials including, but not limited to structural foam, steel, wood, plastics, membranes, glass, ceramic, tile, porcelain, concrete, bricks, rammed earth, or structural straw bales.

The interior of future embodiments can be, but are not limited to, polymerized modified thinset, brick and mortar, ceramic tiles, fiberglass, resins, cedar wood or other varieties, granite or other stone tile, tempered glass tile, Himalayan salt blocks, ice or unglazed tile.

Future embodiments can have legs of different materials and forms such as, but not limited to steel, aluminum, boulders, block legs, wooden legs, legs that can be integrated into the chamber's form such that no legs are visibly seen as separate from the overall form of the chamber. It should be noted that using structural steel to form a base created the feasibility of the bottom entry chamber. The necessary element is that the ingress and egress point is on the floor or bottom 1 of the interior chamber 10, such that little heat escapes when people enter or exit the structure. In the case of the current embodiment, a one-foot tall wooden block is used for those who prefer an extra step up. Future embodiments can utilize this solution, or adopt any series of stepping points as the form, scale and code require.

Future embodiments of a bottom entry sauna, steam room, steam egg or therapeutic room can be utilized for any therapeutic environment that benefits from a bottom entry, such as, but not limited to dry heat, wet heat, aromatherapy.

Future embodiments of the invention can have various methods of evacuating hot or moist air as needed besides those mentioned in the current embodiment, such that there can be holes that have plugs in them like a wine bottle's cork or translucent material instead of the towels used in the current embodiment. The prior art, U.S. Pat. No. 5,628,073, uses a series of sealing rings as vents, that could be utilized in future embodiments of the current advancement.

Future embodiments can be designed for interior or exterior environments. Embodiments can be designed for hot weather climates or cold weather climates. In cases of extreme weather climates such as the winter in higher latitudes or altitudes it will be so cold, that a hinged and vented door with Velcro may be necessary to close the bottom ingress and egress point 1; this future embodiment is within the spirit and intention of the bottom entry therapeutic chambers. Also, a simple weather proof Velcro closure for both the upper 2 and lower apertures 1 to keep the chamber clean, keeps within the intention of the invention.

The best mode contemplated to carry out the invention is by promoting the use of the initial embodiment, Steam Egg. Communal sweating, in the form of dry and wet saunas is becoming ever more popular. There is a real interest thus far in the use of the embodiment shown in the figures. Saunas that can be entered from below, that are freestanding, that are surfaced on the exterior in mirrors or with other site specific surfaces, that have rotating scents and sounds, and that can be in the form of an egg or other form are attractive to those many hundreds of people who have repeatedly used the present embodiment. Private individuals, families and businesses like Korean Bath Houses (Jimjilbang) are ideal consumers of this advancement on the prior art. It can be imagined that a dozen or so bottom entry therapeutic chambers in the same location, with different forms, scales, and methods of therapy could make a successful business plan, similar to that of the Korean Jimjilbang—for example, but not in a limiting form, one bottom entry chamber could house a superheated sauna, while another could be a larger and less hot dry sauna, another could be eucalyptus steam, another could be mugwort steam, another could be for chromotherapy, another strictly for aromatherapy without heat, another could house a vibratory bench, another could house walls made of Himalayan rock salt, another could house a very low temperature or cold room, another could play low frequency sounds, and another could utilize video projections of any variety of image. The bottom entry therapeutic chamber has potential to make steam rooms and saunas as popular in people's backyards as are hot tubs due to the possibilities of form, ease of mass production, its 360-degree seating, and the overall experience of entering from below. Additionally, the ease of cleaning, care and energy costs of a bottom entry sauna compared to the high costs of chemicals, heating and structural strength required for large volumes of water in a hot tub makes the field of bottom entry saunas attractive.

Many changes could be made in the above construction, and many apparently widely different embodiments of this invention could be made without departing from the scope of the claims. It is intended that all matter contained in the above description or shown in the accompanying drawings shall be interpreted as illustrative and not in a limited sense.

What I claim as my invention is:

1. A bottom entry therapeutic room, the bottom entry therapeutic comprising:
   a therapeutic room having an external surface and an interior, the therapeutic room comprising a point of ingress/egress located on a bottom portion of the therapeutic room, the therapeutic room further comprising a height that is larger in dimension than a diameter of the therapeutic room;
   a plurality of legs that are each coupled to the therapeutic room, the plurality of legs configured to elevate the point of ingress/egress so as to facilitate the ingress/egress of a user of the therapeutic room;
   the interior of the therapeutic room comprising a bench seat that is positioned about a circumference of the interior, the interior of the therapeutic room further comprising a vent, the vent configured to alter temperature conditions present within the therapeutic room; and
   a top aperture located on a top portion of the therapeutic room, the top aperture configured to be selectively opened or covered so as to facilitate the altering of the temperature conditions present within the therapeutic room.

2. The bottom entry therapeutic room of claim 1, wherein an interior surface of the interior of the therapeutic room comprises a molded surface.

3. The bottom entry therapeutic room of claim 2, wherein the molded surface provides for a smooth rounded form for the interior of the therapeutic room.

4. The bottom entry therapeutic room of claim 3, wherein the molded surface comprises a combination of mesh material and mortar.

5. The bottom entry therapeutic room of claim 1, wherein the external surface of the therapeutic room comprises a faceted external surface.

6. The bottom entry therapeutic room of claim 5, wherein the faceted external surface comprises a plurality of mirrored surfaces.

7. The bottom entry therapeutic room of claim 1, wherein the top aperture further comprises a removable covering, the removable covering enabling the top aperture to be selectively opened or covered.

8. The bottom entry therapeutic room of claim 1, wherein use of the point of ingress/egress located on the bottom portion of the therapeutic room facilitates ingress/egress of the user without substantially altering the temperature conditions present within the therapeutic room.

9. The bottom entry therapeutic room of claim 8, wherein the therapeutic room comprises a sauna and the vent is configured to transfer heat into the interior of the therapeutic room.

10. The bottom entry therapeutic room of claim 9, wherein the vent is positioned underneath the bench seat.

11. The bottom entry therapeutic room of claim 9, wherein the vent is configured to be coupled to a heat source located external to the therapeutic room.

12. The bottom entry therapeutic room of claim 1, wherein the bench seat is positioned 360° about the diameter of the therapeutic room.

13. The bottom entry therapeutic room of claim 1, further comprising a sauna heating element coupled to the vent, the sauna heating element positioned within the interior of the therapeutic room.

14. The bottom entry therapeutic room of claim 1, further comprising one or more of plumbing and/or electrical wiring disposed within a wall of the therapeutic room.

15. The bottom entry therapeutic room of claim 1, wherein the plurality of legs are configured to elevate the point of ingress/egress to approximately three feet off a ground structure where the bottom entry therapeutic room is located.

16. The bottom entry therapeutic room of claim 15, wherein the plurality of legs are removable thereby facilitating transportation of the therapeutic room from one location to a second different location.

17. The bottom entry therapeutic room of claim 1, wherein the vent is further configured to introduce steam into the interior of the therapeutic room.

18. The bottom entry therapeutic room of claim 17, wherein the vent is further configured to provide aromatherapy into the interior of the therapeutic room.

* * * * *